United States Patent
Wright et al.

(10) Patent No.: US 9,938,217 B2
(45) Date of Patent: Apr. 10, 2018

(54) FLUIDIZED BED MEMBRANE REACTOR

(71) Applicant: RES USA, LLC, Westminster, CO (US)

(72) Inventors: Harold A. Wright, Longmont, CO (US); Mark K. Robertson, Denver, CO (US); Weibin Jiang, Englewood, CO (US)

(73) Assignee: RES USA, LLC, Westminster, CO (US)

( * ) Notice: Subject to any disclaimer, the term of this patent is extended or adjusted under 35 U.S.C. 154(b) by 0 days.

(21) Appl. No.: 15/612,350

(22) Filed: Jun. 2, 2017

(65) Prior Publication Data

US 2018/0002263 A1    Jan. 4, 2018

Related U.S. Application Data

(60) Provisional application No. 62/357,524, filed on Jul. 1, 2016.

(51) Int. Cl.
    *C07C 41/01* (2006.01)
    *B01J 21/04* (2006.01)
    (Continued)

(52) U.S. Cl.
    CPC .............. *C07C 41/01* (2013.01); *B01J 8/1827* (2013.01); *B01J 8/1872* (2013.01); *B01J 21/04* (2013.01);
    (Continued)

(58) Field of Classification Search
    CPC .............. C01B 3/34; C01B 2203/0238; C01B 2203/04; C01B 2203/0405; C07C 41/01; C07C 1/22; C07C 43/043
    See application file for complete search history.

(56) References Cited

U.S. PATENT DOCUMENTS

| 4,218,388 A | 8/1980 | Schaper et al. |
| 4,337,176 A | 6/1982 | Boersma et al. |

(Continued)

FOREIGN PATENT DOCUMENTS

| CA | 1042925 A | 11/1978 |
| CA | 1046513 A | 1/1979 |

(Continued)

OTHER PUBLICATIONS

M.E.E. Abashar , Coupling of steam and dry reforming of methane in catalytic fluidized bed membrane reactors, International Journal of Hydrogen Energy 29 (2004) 799-808.*
(Continued)

*Primary Examiner* — Jafar Parsa
(74) *Attorney, Agent, or Firm* — Timothy S. Westby; Porter Hedges LLP

(57) ABSTRACT

Herein disclosed is a dry reforming reactor comprising a gas inlet near the bottom of the reactor; a gas outlet near the top of the reactor; a fluidized bed comprising a catalyst; and one or more hydrogen membranes comprising palladium (Pd). In some cases, the one or more hydrogen membranes comprises Pd alloy membranes, or Pd supported on ceramics or metals. In some cases, the one or more hydrogen membranes are placed vertically in the reactor as hydrogen membrane tubes hanging from the top of the reactor. In some cases, the hydrogen membranes are configured to selectively collect hydrogen from the tubes via one or more internal manifolds and sent to an external hydrogen collection system.

14 Claims, 5 Drawing Sheets

(51) Int. Cl.
*C01B 3/44* (2006.01)
*C01B 3/50* (2006.01)
*B01J 23/755* (2006.01)
*B01J 8/18* (2006.01)

(52) U.S. Cl.
CPC ............. *B01J 23/755* (2013.01); *C01B 3/44* (2013.01); *C01B 3/505* (2013.01); *B01J 2208/00991* (2013.01); *C01B 2203/0238* (2013.01); *C01B 2203/041* (2013.01); *C01B 2203/06* (2013.01); *C01B 2203/1058* (2013.01); *C01B 2203/1082* (2013.01); *C01B 2203/1241* (2013.01)

(56) References Cited

U.S. PATENT DOCUMENTS

| | | |
|---|---|---|
| 4,338,089 A | 7/1982 | Schaper et al. |
| 4,349,464 A | 9/1982 | Wainwright et al. |
| 4,366,260 A | 12/1982 | Wainwright et al. |
| 4,385,193 A | 5/1983 | Bijwaard et al. |
| 4,403,044 A | 9/1983 | Post et al. |
| 4,433,065 A | 2/1984 | van der Burgt et al. |
| 4,443,561 A | 4/1984 | Boelema et al. |
| 4,523,046 A | 6/1985 | Gould et al. |
| 4,616,098 A | 10/1986 | Hoelderich et al. |
| 5,177,290 A | 1/1993 | Ryu et al. |
| 5,189,203 A | 2/1993 | Hansen et al. |
| 5,218,003 A | 6/1993 | Lewnard et al. |
| 5,254,596 A | 10/1993 | Irick, Jr. et al. |
| 5,286,900 A | 2/1994 | Hansen et al. |
| 5,326,550 A | 7/1994 | Adris et al. |
| 5,359,118 A | 10/1994 | Wagner et al. |
| 5,389,689 A | 2/1995 | Fujimoto et al. |
| 5,392,594 A | 2/1995 | Moore et al. |
| 5,466,720 A | 11/1995 | Fujimoto et al. |
| 5,502,243 A | 3/1996 | Waller et al. |
| 5,666,800 A | 9/1997 | Sorensen et al. |
| 5,728,871 A | 3/1998 | Joensen et al. |
| 5,744,636 A | 4/1998 | Ramprasad et al. |
| 5,753,716 A | 5/1998 | Peng et al. |
| 5,763,654 A | 6/1998 | Jones et al. |
| 5,840,969 A | 11/1998 | Joensen |
| 5,865,023 A | 2/1999 | Sorensen et al. |
| 5,892,110 A | 4/1999 | Ramprasad et al. |
| 5,908,963 A | 6/1999 | Voss et al. |
| 6,069,180 A | 5/2000 | Peng et al. |
| 6,147,125 A | 11/2000 | Shikada et al. |
| 6,191,175 B1 | 2/2001 | Haugaard et al. |
| 6,211,254 B1 | 4/2001 | Whitney |
| 6,331,283 B1 | 12/2001 | Roy et al. |
| 6,452,058 B1 | 9/2002 | Schweizer et al. |
| 6,458,856 B1 | 10/2002 | Peng et al. |
| 6,458,995 B1 | 10/2002 | Cheung et al. |
| 6,476,084 B2 | 11/2002 | Whitney |
| 6,521,783 B1 | 2/2003 | Wegman et al. |
| 6,562,306 B1 | 5/2003 | Shikada et al. |
| 6,608,114 B1 | 8/2003 | Heydom et al. |
| 6,627,770 B1 | 9/2003 | Cheung et al. |
| 6,642,280 B2 | 11/2003 | Sorensen et al. |
| 6,656,978 B2 | 12/2003 | Shiroto et al. |
| 6,753,108 B1 | 6/2004 | Hampden-Smith et al. |
| 6,800,665 B1 | 10/2004 | Shikada et al. |
| 6,806,296 B2 | 10/2004 | Shiroto et al. |
| 6,967,183 B2 | 11/2005 | Hampden-Smith et al. |
| 6,991,754 B2 | 1/2006 | Hampden-Smith et al. |
| 7,029,515 B2 | 4/2006 | Krueger |
| 7,033,972 B2 | 4/2006 | Shikada et al. |
| 7,087,341 B2 | 8/2006 | Hampden-Smith et al. |
| 7,100,692 B2 | 9/2006 | Parsley et al. |
| 7,138,159 B2 | 11/2006 | Hampden-Smith et al. |
| 7,211,345 B2 | 5/2007 | Hampden-Smith et al. |
| 7,417,004 B2 | 8/2008 | Jun et al. |
| 7,432,410 B2 | 10/2008 | Asami et al. |
| 7,435,759 B2 | 10/2008 | Jung et al. |
| 7,507,687 B2 | 3/2009 | Kodas et al. |
| 7,517,374 B2 | 4/2009 | Nielsen et al. |
| 7,589,246 B2 | 9/2009 | Iaccino et al. |
| 7,605,293 B2 | 10/2009 | Olah et al. |
| 7,608,743 B2 | 10/2009 | Olah et al. |
| 7,659,437 B2 | 2/2010 | Iaccino et al. |
| 7,683,227 B2 | 3/2010 | Iaccino et al. |
| 7,704,369 B2 | 4/2010 | Olah et al. |
| 7,705,059 B2 | 4/2010 | Olah et al. |
| 7,722,687 B2 | 5/2010 | Hampden-Smith et al. |
| 7,728,046 B2 | 6/2010 | Fujimoto et al. |
| 7,728,186 B2 | 6/2010 | Iaccino et al. |
| 7,754,930 B2 | 7/2010 | Iaccino |
| 7,759,535 B2 | 7/2010 | Iaccino et al. |
| 7,772,447 B2 | 8/2010 | Iaccino et al. |
| 7,772,450 B2 | 8/2010 | Iaccino et al. |
| 7,781,636 B2 | 8/2010 | Iaccino et al. |
| 7,795,490 B2 | 9/2010 | Iaccino et al. |
| 7,834,230 B2 | 11/2010 | Fujimoto et al. |
| 7,846,978 B2 | 12/2010 | Olah et al. |
| 7,867,957 B2 | 1/2011 | Matsui et al. |
| 7,880,049 B2 | 2/2011 | Dumesic et al. |
| 7,888,543 B2 | 2/2011 | Iaccino et al. |
| 7,893,308 B2 | 2/2011 | Sangar et al. |
| 7,906,559 B2 | 3/2011 | Olah et al. |
| 7,915,196 B2 | 3/2011 | Parent et al. |
| 7,951,985 B2 | 5/2011 | Sangar et al. |
| 7,968,759 B2 | 6/2011 | Iaccino et al. |
| 7,977,519 B2 | 7/2011 | Iaccino et al. |
| 7,982,080 B2 | 7/2011 | Xu et al. |
| 8,003,841 B2 | 8/2011 | Bozzano |
| 8,084,641 B2 | 12/2011 | Wang |
| 8,133,926 B2 | 3/2012 | Olah et al. |
| 8,138,380 B2 | 3/2012 | Olah et al. |
| 8,138,384 B2 | 3/2012 | Iaccino et al. |
| 8,148,553 B2 | 4/2012 | Dumesic et al. |
| 8,198,479 B2 | 6/2012 | Arhancet et al. |
| 8,212,088 B2 | 7/2012 | Olah et al. |
| 8,257,661 B2 | 9/2012 | Bozzano |
| 8,277,631 B2 | 10/2012 | Eastman et al. |
| 8,283,490 B2 | 10/2012 | Ditzel et al. |
| 8,288,594 B2 | 10/2012 | Stites et al. |
| 8,378,150 B2 | 2/2013 | Loescher |
| 8,394,983 B2 | 3/2013 | Ditzel et al. |
| 8,409,307 B2 | 4/2013 | Drnevich et al. |
| 8,440,729 B2 | 5/2013 | Olah et al. |
| 8,440,872 B2 | 5/2013 | Buchanan et al. |
| 8,450,521 B2 | 5/2013 | Ditzel et al. |
| 8,471,058 B2 | 6/2013 | Ditzel et al. |
| 8,536,369 B2 | 9/2013 | Ditzel et al. |
| 8,536,385 B2 | 9/2013 | Okuyama et al. |
| 8,546,454 B2 | 10/2013 | Randhava et al. |
| 8,552,074 B2 | 10/2013 | Fu et al. |
| 8,552,216 B2 | 10/2013 | Deeley et al. |
| 8,624,043 B2 | 1/2014 | Dumesic et al. |
| 8,624,054 B2 | 1/2014 | Hazel et al. |
| 8,669,295 B2 | 3/2014 | Fu et al. |
| 8,669,383 B2 | 3/2014 | Howard et al. |
| 8,691,881 B2 | 4/2014 | Kauchali |
| 8,715,980 B2 | 5/2014 | Clarke |
| 8,748,500 B2 | 6/2014 | Goetsch et al. |
| 8,791,165 B2 | 7/2014 | Randhava et al. |
| 8,841,227 B2 | 9/2014 | Sangar et al. |
| 8,859,835 B2 | 10/2014 | Clem et al. |
| 8,901,326 B2 | 12/2014 | Howard et al. |
| 8,957,259 B2 | 2/2015 | Dagle et al. |
| 8,962,513 B2 | 2/2015 | Liu et al. |
| 8,975,450 B2 | 3/2015 | Scates |
| 8,980,196 B2 | 3/2015 | Zmierczak et al. |
| 8,980,961 B2 | 3/2015 | Olah et al. |
| 9,034,208 B1 | 5/2015 | Agee |
| 9,067,903 B2 | 6/2015 | Dumesic et al. |
| 9,090,543 B2 | 7/2015 | Schoedel et al. |
| 9,206,360 B2 | 12/2015 | Do et al. |
| 9,242,920 B2 | 1/2016 | Bristow |
| 9,249,078 B2 | 2/2016 | Wang et al. |
| 9,295,978 B2 | 3/2016 | Schafer et al. |
| 9,296,665 B2 | 3/2016 | Kortan et al. |
| 9,315,910 B2 | 4/2016 | Eastman et al. |

(56) References Cited

U.S. PATENT DOCUMENTS

| | | |
|---|---|---|
| 9,321,783 B2 | 4/2016 | Ibert et al. |
| 9,376,360 B2 | 6/2016 | Ahlers et al. |
| 9,379,421 B2 | 6/2016 | Garsuch et al. |
| 9,393,555 B2 | 7/2016 | Schafer et al. |
| 9,409,846 B2 | 8/2016 | Torrence |
| 9,422,494 B2 | 8/2016 | Bradin |
| 9,469,591 B2 | 10/2016 | Bristow |
| 9,481,624 B2 | 11/2016 | Loescher |
| 9,493,709 B2 | 11/2016 | Goerz, Jr. |
| 9,499,470 B2 | 11/2016 | Ditzel et al. |
| 9,504,978 B2 | 11/2016 | Ahlers et al. |
| 9,505,702 B2 | 11/2016 | Becker et al. |
| 9,505,703 B2 | 11/2016 | Ditzel et al. |
| 9,546,120 B2 | 1/2017 | Bristow |
| 9,567,542 B2 | 2/2017 | Goerz, Jr. |
| 9,598,347 B2 | 3/2017 | Ditzel et al. |
| 9,610,568 B2 | 4/2017 | Schafer et al. |
| 9,643,906 B2 | 5/2017 | Zubrin et al. |
| 9,682,900 B2 | 6/2017 | Keusenkothen et al. |
| 9,695,097 B2 | 7/2017 | Salciccioli et al. |
| 9,758,460 B2 | 9/2017 | Kumar et al. |
| 2001/0020044 A1 | 9/2001 | Whitney |
| 2002/0107140 A1 | 8/2002 | Hampden-Smith et al. |
| 2003/0036572 A1 | 2/2003 | Shiroto et al. |
| 2003/0039600 A1 | 2/2003 | Sorensen et al. |
| 2003/0049517 A1 | 3/2003 | Hampden-Smith et al. |
| 2003/0054218 A1 | 3/2003 | Hampden-Smith et al. |
| 2003/0064265 A1 | 4/2003 | Hampden-Smith et al. |
| 2003/0103893 A1 | 6/2003 | de Lasa et al. |
| 2003/0118884 A1 | 6/2003 | Hampden-Smith et al. |
| 2003/0130114 A1 | 7/2003 | Hampden-Smith et al. |
| 2004/0048936 A1 | 3/2004 | Shiroto et al. |
| 2004/0072683 A1 | 4/2004 | Kodas et al. |
| 2004/0244973 A1 | 12/2004 | Parsley et al. |
| 2005/0038129 A1 | 2/2005 | Shikada et al. |
| 2006/0013762 A1 | 1/2006 | Kuipers et al. |
| 2006/0020155 A1 | 1/2006 | Beech et al. |
| 2006/0036122 A1 | 2/2006 | Asami et al. |
| 2006/0052647 A1 | 3/2006 | Shikada et al. |
| 2006/0120953 A1 | 6/2006 | Okuyama et al. |
| 2006/0168888 A1 | 8/2006 | Nielsen et al. |
| 2006/0229466 A1 | 10/2006 | Arhancet et al. |
| 2006/0235088 A1 | 10/2006 | Olah et al. |
| 2006/0235091 A1 | 10/2006 | Olah et al. |
| 2006/0247122 A1 | 11/2006 | Hampden-Smith et al. |
| 2007/0078285 A1 | 4/2007 | Dagle et al. |
| 2007/0106106 A1 | 5/2007 | Fujimoto et al. |
| 2007/0117709 A1 | 5/2007 | Jun et al. |
| 2007/0129587 A1 | 6/2007 | Iaccino et al. |
| 2007/0142482 A1 | 6/2007 | Jung et al. |
| 2007/0249740 A1 | 10/2007 | Iaccino et al. |
| 2007/0249879 A1 | 10/2007 | Iaccino et al. |
| 2007/0249880 A1 | 10/2007 | Iaccino et al. |
| 2007/0254969 A1 | 11/2007 | Olah et al. |
| 2007/0260098 A1 | 11/2007 | Iaccino et al. |
| 2007/0276171 A9 | 11/2007 | Iaccino et al. |
| 2007/0277552 A1 | 12/2007 | Fujimoto et al. |
| 2007/0282019 A1 | 12/2007 | Fujimoto et al. |
| 2007/0282145 A1 | 12/2007 | Iaccino et al. |
| 2007/0293709 A1 | 12/2007 | Iaccino et al. |
| 2008/0021251 A1 | 1/2008 | Iaccino et al. |
| 2008/0027150 A1 | 1/2008 | Steynberg |
| 2008/0047872 A1 | 2/2008 | Iaccino et al. |
| 2008/0051617 A1 | 2/2008 | Sangar et al. |
| 2008/0058564 A1 | 3/2008 | Iaccino et al. |
| 2008/0113257 A1 | 5/2008 | Hampden-Smith et al. |
| 2008/0248981 A1 | 10/2008 | Matsui et al. |
| 2008/0249342 A1 | 10/2008 | Iaccino et al. |
| 2008/0283411 A1 | 11/2008 | Eastman et al. |
| 2008/0300327 A1 | 12/2008 | Fujimoto et al. |
| 2008/0319093 A1 | 12/2008 | Olah et al. |
| 2009/0014336 A1 | 1/2009 | Olah et al. |
| 2009/0030240 A1 | 1/2009 | Olah et al. |
| 2009/0030253 A1 | 1/2009 | Xu et al. |
| 2009/0088588 A1 | 4/2009 | Wang |
| 2009/0093657 A1 | 4/2009 | Buchanan et al. |
| 2009/0124839 A1 | 5/2009 | Dumesic et al. |
| 2009/0130502 A1 | 5/2009 | Liu et al. |
| 2009/0230024 A1 | 9/2009 | Steynberg et al. |
| 2009/0264543 A1 | 10/2009 | Xu et al. |
| 2009/0292149 A1 | 11/2009 | Li et al. |
| 2009/0293348 A1 | 12/2009 | Olah et al. |
| 2009/0326281 A1 | 12/2009 | Appel et al. |
| 2009/0326298 A1 | 12/2009 | Bozzano |
| 2010/0000153 A1 | 1/2010 | Kurkjian et al. |
| 2010/0063315 A1 | 3/2010 | Ditzel et al. |
| 2010/0099935 A1 | 4/2010 | Iaccino et al. |
| 2010/0121098 A1 | 5/2010 | Ditzel et al. |
| 2010/0121099 A1 | 5/2010 | Deeley et al. |
| 2010/0130771 A1 | 5/2010 | Ditzel et al. |
| 2010/0152474 A1 | 6/2010 | Olah et al. |
| 2010/0193370 A1 | 8/2010 | Olah et al. |
| 2010/0216897 A1 | 8/2010 | Rostrup-Nielsen |
| 2010/0240935 A1 | 9/2010 | Iaccino et al. |
| 2010/0240938 A1 | 9/2010 | Daniel et al. |
| 2010/0305374 A1 | 12/2010 | Iaccino et al. |
| 2010/0317747 A1 | 12/2010 | Okuyarna et al. |
| 2010/0324310 A1 | 12/2010 | Dumesic et al. |
| 2010/0331592 A1 | 12/2010 | Sangar et al. |
| 2011/0028307 A1 | 2/2011 | Fujimoto et al. |
| 2011/0040129 A1 | 2/2011 | Loescher |
| 2011/0040135 A1 | 2/2011 | Iaccino et al. |
| 2011/0054045 A1 | 3/2011 | Olah et al. |
| 2011/0054232 A1 | 3/2011 | Sangar et al. |
| 2011/0092726 A1 | 4/2011 | Clarke |
| 2011/0105306 A1 | 5/2011 | Chien et al. |
| 2011/0105816 A1 | 5/2011 | Sangar et al. |
| 2011/0124927 A1 | 5/2011 | Stites et al. |
| 2011/0177410 A1 | 7/2011 | Assink et al. |
| 2011/0218356 A1 | 9/2011 | Ditzel et al. |
| 2011/0237825 A1 | 9/2011 | Ditzel et al. |
| 2011/0268622 A1 | 11/2011 | Bozzano |
| 2011/0319654 A1 | 12/2011 | Hazel et al. |
| 2012/0083539 A1 | 4/2012 | Fu et al. |
| 2012/0083637 A1 | 4/2012 | Clem et al. |
| 2012/0115965 A1 | 5/2012 | Olah et al. |
| 2012/0115966 A1 | 5/2012 | Fu et al. |
| 2012/0149922 A1 | 6/2012 | Dumesic et al. |
| 2012/0149944 A1 | 6/2012 | Zmierczak et al. |
| 2012/0157554 A1 | 6/2012 | Okuyama et al. |
| 2012/0220804 A1 | 8/2012 | Mitschke et al. |
| 2012/0264595 A1 | 10/2012 | Arhancet et al. |
| 2012/0277328 A1 | 11/2012 | Kauchali |
| 2012/0277330 A1 | 11/2012 | Goetsch et al. |
| 2012/0297665 A1 | 11/2012 | Goerz, Jr. |
| 2012/0329657 A1 | 12/2012 | Eastman et al. |
| 2013/0035406 A1 | 2/2013 | Randhava et al. |
| 2013/0184498 A1 | 7/2013 | Loescher |
| 2013/0210612 A1 | 8/2013 | Schafer et al. |
| 2013/0210940 A1 | 8/2013 | Schafer et al. |
| 2013/0211147 A1 | 8/2013 | Cheiky et al. |
| 2013/0211148 A1 | 8/2013 | Schafer et al. |
| 2013/0303791 A1 | 11/2013 | Howard et al. |
| 2014/0017577 A1 | 1/2014 | Minami et al. |
| 2014/0094618 A1 | 4/2014 | Dumesic et al. |
| 2014/0148605 A1 | 5/2014 | Howard et al. |
| 2014/0171691 A1 | 6/2014 | Kortan et al. |
| 2014/0194662 A1 | 7/2014 | Nesterenko et al. |
| 2014/0243568 A1 | 8/2014 | Nesterenko et al. |
| 2014/0243570 A1 | 8/2014 | Nesterenko et al. |
| 2014/0275620 A1 | 9/2014 | Torrence |
| 2014/0275641 A1 | 9/2014 | Scates |
| 2014/0296599 A1 | 10/2014 | Nesterenko et al. |
| 2014/0316177 A1 | 10/2014 | Ge et al. |
| 2014/0364654 A1 | 12/2014 | Randhava et al. |
| 2015/0018582 A1 | 1/2015 | Schodel et al. |
| 2015/0018592 A1 | 1/2015 | Schodel et al. |
| 2015/0038745 A1 | 2/2015 | Ahlers et al. |
| 2015/0045456 A1 | 2/2015 | Schoedel et al. |
| 2015/0047252 A1 | 2/2015 | Goerz, Jr. |
| 2015/0072400 A1 | 3/2015 | Clarke |
| 2015/0099196 A1 | 4/2015 | Garsuch et al. |
| 2015/0105479 A1 | 4/2015 | Schafer et al. |
| 2015/0148567 A1 | 5/2015 | Wang et al. |

(56) References Cited

U.S. PATENT DOCUMENTS

| | | | |
|---|---|---|---|
| 2015/0158792 A1 | 6/2015 | Keusenkothen et al. |
| 2015/0165408 A1 | 6/2015 | Zmierczak et al. |
| 2015/0175512 A1 | 6/2015 | Ahlers et al. |
| 2015/0191666 A1 | 7/2015 | Bradin |
| 2015/0203507 A1 | 7/2015 | Ibert et al. |
| 2015/0247100 A1 | 9/2015 | Bradin |
| 2015/0299594 A1 | 10/2015 | Hinnemann et al. |
| 2015/0329450 A1 | 11/2015 | Bristow |
| 2015/0329465 A1 | 11/2015 | Becker et al. |
| 2015/0329466 A1 | 11/2015 | Bristow |
| 2015/0336868 A1 | 11/2015 | Bristow |
| 2015/0353840 A1 | 12/2015 | Hensley et al. |
| 2016/0009629 A1 | 1/2016 | Ditzel et al. |
| 2016/0016155 A1 | 1/2016 | Sunley |
| 2016/0016881 A1 | 1/2016 | Ditzel et al. |
| 2016/0052857 A1 | 2/2016 | Ditzel et al. |
| 2016/0096168 A1 | 4/2016 | Sangar et al. |
| 2016/0152537 A1 | 6/2016 | Zubrin et al. |
| 2016/0158734 A1 | 6/2016 | Shen et al. |
| 2016/0168477 A1 | 6/2016 | Kortan et al. |
| 2016/0194766 A1 | 7/2016 | Eastman et al. |
| 2016/0308220 A1 | 10/2016 | Qi et al. |
| 2016/0311740 A1 | 10/2016 | Liu et al. |
| 2016/0318006 A1 | 11/2016 | Malyala et al. |
| 2016/0347697 A1 | 12/2016 | Kumar et al. |
| 2016/0362355 A1 | 12/2016 | Liang et al. |
| 2017/0009165 A1 | 1/2017 | Goerz, Jr. |
| 2017/0022129 A1 | 1/2017 | Salciccioli et al. |
| 2017/0081271 A1 | 3/2017 | Bristow |
| 2017/0088495 A1 | 3/2017 | Bristow |
| 2017/0113981 A1 | 4/2017 | Mukherjee et al. |
| 2017/0121264 A1 | 5/2017 | Bristow |
| 2017/0152453 A1 | 6/2017 | Goerz |
| 2017/0174599 A1 | 6/2017 | Zubrin et al. |
| 2017/0203281 A1 | 7/2017 | Asthana et al. |
| 2017/0210679 A1 | 7/2017 | Chojecki et al. |
| 2017/0247300 A1 | 8/2017 | Keusenkothen et al. |
| 2017/0253539 A1 | 9/2017 | Fournier et al. |

FOREIGN PATENT DOCUMENTS

| | | |
|---|---|---|
| CA | 1052780 A | 4/1979 |
| CA | 1058225 A | 7/1979 |
| CA | 1058636 A | 7/1979 |
| CA | 1065885 A | 11/1979 |
| CA | 1102356 A | 6/1981 |
| CA | 1106371 A | 8/1981 |
| CA | 1117061 A | 1/1982 |
| CA | 1121834 A | 4/1982 |
| CA | 1122620 A | 4/1982 |
| CA | 1127671 A | 7/1982 |
| CA | 1128964 A | 8/1982 |
| CA | 1153354 A | 9/1983 |
| CA | 1154737 A | 10/1983 |
| CA | 1156265 A | 11/1983 |
| CA | 1157484 A | 11/1983 |
| CA | 1172270 A | 8/1984 |
| CA | 1192891 A | 9/1985 |
| CA | 1205093 A | 5/1986 |
| CA | 1210749 A | 9/1986 |
| CA | 1220229 A | 4/1987 |
| CA | 1224488 A | 7/1987 |
| CA | 1253882 A | 5/1989 |
| CA | 1260019 A | 9/1989 |
| CA | 2007813 A1 | 7/1990 |
| CA | 2016187 A1 | 11/1990 |
| CA | 2020929 A1 | 1/1991 |
| CA | 2050570 A1 | 3/1992 |
| CA | 2043779 A1 | 4/1992 |
| CA | 2053615 A1 | 4/1992 |
| CA | 2053828 A1 | 5/1992 |
| CA | 1304749 C | 7/1992 |
| CA | 1305464 C | 7/1992 |
| CA | 2066907 A1 | 10/1992 |
| CA | 2066916 A1 | 10/1992 |
| CA | 2067642 A1 | 12/1992 |
| CA | 2073324 A1 | 1/1993 |
| CA | 2065088 A1 | 9/1993 |
| CA | 2093752 A1 | 10/1993 |
| CA | 1330249 C | 6/1994 |
| CA | 2114205 A1 | 8/1994 |
| CA | 1332597 C | 10/1994 |
| CA | 2194140 A1 | 1/1996 |
| CA | 2158006 A1 | 3/1996 |
| CA | 2182294 A1 | 6/1996 |
| CA | 2211722 A1 | 8/1996 |
| CA | 2170823 A1 | 9/1996 |
| CA | 2188217 A1 | 4/1997 |
| CA | 2239017 A1 | 6/1997 |
| CA | 2247442 A1 | 9/1997 |
| CA | 2205282 A1 | 11/1997 |
| CA | 2205316 A1 | 11/1997 |
| CA | 2207353 A1 | 6/1998 |
| CA | 2229474 A1 | 8/1998 |
| CA | 2228738 A1 | 8/1999 |
| CA | 2249126 A1 | 4/2000 |
| CA | 2249126 A1 | 4/2000 |
| CA | 2370994 A1 | 12/2000 |
| CA | 2368496 A1 | 9/2001 |
| CA | 2404977 A1 | 11/2001 |
| CA | 2415926 A1 | 1/2002 |
| CA | 2417149 A1 | 2/2002 |
| CA | 2447761 A1 | 11/2002 |
| CA | 2458905 A1 | 3/2003 |
| CA | 2476867 A1 | 8/2003 |
| CA | 2511998 A1 | 7/2004 |
| CA | 2519118 A1 | 10/2004 |
| CA | 2538124 A1 | 12/2004 |
| CA | 2532874 A1 | 2/2005 |
| CA | 2554221 A1 | 9/2005 |
| CA | 2559527 A1 | 9/2005 |
| CA | 2562392 A1 | 11/2005 |
| CA | 2508980 A1 | 12/2005 |
| CA | 2589269 A1 | 6/2006 |
| CA | 2589467 A1 | 6/2006 |
| CA | 2590833 A1 | 6/2006 |
| CA | 2601124 A1 | 9/2006 |
| CA | 2613097 A1 | 1/2007 |
| CA | 2613483 A1 | 1/2007 |
| CA | 2613497 A1 | 1/2007 |
| CA | 2616303 A1 | 2/2007 |
| CA | 2619539 A1 | 2/2007 |
| CA | 2633135 A1 | 6/2007 |
| CA | 2635224 A1 | 7/2007 |
| CA | 2623390 A1 | 8/2007 |
| CA | 2637904 A1 | 10/2007 |
| CA | 2648176 A1 | 10/2007 |
| CA | 2653928 A1 | 12/2007 |
| CA | 2682271 A1 | 10/2008 |
| CA | 2684638 A1 | 10/2008 |
| CA | 2684071 A1 | 11/2008 |
| CA | 2684548 A1 | 11/2008 |
| CA | 2684558 A1 | 11/2008 |
| CA | 2690836 A1 | 12/2008 |
| CA | 2738270 A1 | 10/2009 |
| CA | 2728322 A1 | 12/2009 |
| CA | 2728314 A1 | 1/2010 |
| CA | 2739975 A1 | 4/2010 |
| CA | 2740301 A1 | 4/2010 |
| CA | 2756416 A1 | 10/2010 |
| CA | 2756753 A1 | 10/2010 |
| CA | 2757577 A1 | 10/2010 |
| CA | 2764341 A1 | 12/2010 |
| CA | 2768377 A1 | 1/2011 |
| CA | 2739274 A1 | 9/2011 |
| CA | 2792325 A1 | 9/2011 |
| CA | 2793768 A1 | 10/2011 |
| CA | 2813368 A1 | 4/2012 |
| CA | 2834979 A1 | 12/2012 |
| CA | 2856691 A1 | 6/2013 |
| CA | 2862796 A1 | 7/2013 |
| CA | 2860876 A1 | 8/2013 |
| CA | 2865968 A1 | 10/2013 |
| CA | 2877165 A1 | 12/2013 |

(56) References Cited

FOREIGN PATENT DOCUMENTS

| | | | |
|---|---|---|---|
| CA | 2882774 | A1 | 3/2014 |
| CA | 2884175 | A1 | 3/2014 |
| CA | 2919360 | A1 | 3/2014 |
| CA | 2886918 | A1 | 5/2014 |
| CA | 2894152 | A1 | 6/2014 |
| CA | 2894283 | A1 | 6/2014 |
| CA | 2894285 | A1 | 6/2014 |
| CA | 2894444 | A1 | 6/2014 |
| CA | 2896678 | A1 | 7/2014 |
| CA | 2902113 | A1 | 10/2014 |
| CA | 2928831 | A1 | 4/2015 |
| CA | 2930135 | A1 | 5/2015 |
| CA | 2933813 | A1 | 8/2015 |
| CA | 2939779 | A1 | 9/2015 |
| CA | 2939782 | A1 | 9/2015 |
| CA | 2949762 | A1 | 1/2016 |
| CA | 2957236 | A1 | 2/2016 |
| CA | 2931633 | A1 | 12/2016 |
| CA | 2943873 | A1 | 4/2017 |
| CN | 1413973 | A | 4/2003 |
| CN | 101837955 | B | 7/2012 |
| CN | 101837955 | B | 7/2012 |
| EP | 1427667 | B1 | 10/2011 |
| EP | 1427667 | B1 | 10/2011 |
| JP | 10259148 | A | 9/1998 |
| WO | 2013044134 | | 3/2013 |
| WO | 2013044134 | A2 | 3/2013 |
| WO | 2013137720 | | 9/2013 |
| WO | 2013137720 | A1 | 9/2013 |
| WO | 2015193186 | A1 | 12/2015 |
| WO | 2015193188 | A1 | 12/2015 |

OTHER PUBLICATIONS

Lukyanov, B. N.; Andreev, D. V.; Parmon, V. N. Catalytic reactors with hydrogen membrane separation. Chem Eng J 2009,154, 258-266.

Song, D; Cho, W.; Park, D.; Yoon, E. Comparison of the Performance of a Fixed Bed Reactor in the Two Cases, Mixture of Catalyst Pellets and a Hybrid Catalyst, for Dimetyl Ether Synthesis. J. Ind. Eng. Chem. 2007, 13, 815-826.

Evenson, C.; Mackay, R.; Faull, J. Final Report: DE-FC26-05NT42469 Scale Up of Hydrogen Separation Membranes; Final Report: DE-FC26-05NT42469; Eltron Research & Development, 2015, 1-188.

Cho, W.; Yu, H.; Mo, Y.; Ahn, W. Experimental Study of Hydrogen and Syngas Production over Ni/Ce—$ZrO_2$/$Al_2O_3$ Catalysts with Additives. Transactions Korean Hydrog New Energy Soc 2014, 25, 105-113.

Suttichai Assabumrungrat et al.; "Fuel Processing Technologies for Hydrogen Production from Methane"; Engineering Journal, vol. 16, Issue 2, Apr. 2012, (4 pgs.).

International Search Report and Written Opinion dated Aug. 31, 2017 for corresponding WO Patent Application No. PCT/US2017/035657, 12 pages.

Hayer, F., et al., "Synthesis of dimethyl ether from syngas in a microchannel reactor-Simulation and experimental study", Chemical Engineering Journal, 2011, vol. 167, pp. 610-615, (see p. 611, left column).

International Search Report and Written Opinion dated Oct. 13, 2017 for corresponding WO Patent Application No. PCT/US2017/035663, 14 pages.

Freni, S. et al., "Hydrogen production from methane through catalytic partial oxidation reactions", Journal of Power Sources, 2000, vol. 87, No. 1, pp. 28-38.

\* cited by examiner

FLUIDIZED BED MEMBRANE REACTOR

CROSS-REFERENCE TO RELATED APPLICATIONS

This application claims the benefit under 35 U.S.C. § 119(e) of U.S. Provisional Patent Applications No. 62/357,524 filed Jul. 1, 2016, the disclosure of which is hereby incorporated herein by reference in its entirety.

STATEMENT REGARDING FEDERALLY SPONSORED RESEARCH OR DEVELOPMENT

Not applicable.

BACKGROUND

Field of the Invention

This disclosure relates generally to fluidized bed membrane reactors. More particularly, this disclosure relates to fluidized bed membrane reactors for dry reforming.

Background of Invention

Dry reforming (also known as carbon dioxide reforming) is a method of producing synthesis gas (mixtures of hydrogen and carbon monoxide) from the reaction of carbon dioxide with hydrocarbons such as methane. Synthesis gas is conventionally produced via the steam reforming reaction. In recent years, increased concerns on the contribution of greenhouse gases (GHG) to global warming have increased interest in the replacement of steam as reactant with carbon dioxide.

The dry reforming reaction may be represented by: $CO_2 + CH_4 \rightarrow 2 H_2 + 2 CO$ Thus, two greenhouse gases are consumed and useful chemical building blocks, hydrogen and carbon monoxide, are produced. A challenge to the commercialization of this process is that the hydrogen that is produced tends to react with the carbon dioxide. For example, the following reaction typically proceeds with a lower activation energy than the dry reforming reaction itself: $CO_2 + H_2 \rightarrow H_2O + CO$. Another challenge to commercialization is that dry reforming reaction is equilibrium limited which means that under most circumstances, the reaction does not go to completion. Another challenge to commercialization is that the equilibrium extent of reaction is limited as the pressure increases. Gas Phase equilibrium reactions, such as the dry reforming reaction that have a net increase in moles of gas across the reaction are favored at lower pressure. Operation at low pressure is disadvantageous due to the higher volume of reactor needed and the higher cost of compression to get the product gas prepared for subsequent use.

As such, there is continuing interest and need to develop new methods and systems for more efficient dry reforming processes.

SUMMARY

Herein disclosed is a dry reforming reactor comprising a gas inlet near the bottom of the reactor; a gas outlet near the top of the reactor; a fluidized bed comprising a catalyst; and one or more hydrogen membranes comprising palladium (Pd). In an embodiment, the one or more hydrogen membranes comprises Pd alloy membranes, or Pd alloys supported on ceramic or metal substrates. In an embodiment, the one or more hydrogen membranes are placed vertically in the reactor as hydrogen membrane tubes hanging from the top of the reactor. In an embodiment, the hydrogen membranes are configured to selectively collect hydrogen from the tubes via one or more internal manifolds and sent to an external hydrogen collection system. In an embodiment, the membrane is coated with an erosion resistant layer.

In an embodiment, the gas inlet is configured to allow one or more feed streams to enter the reactor via a manifold or distributor. In an embodiment, the catalyst in the reactor comprises nickel and alumina. In an embodiment, the one or more feed streams fluidize the catalyst in the reactor. In an embodiment, the reactor is configured to allow reformed gas to exit the top of the reactor and separate from spent catalyst. In an embodiment, no steam or oxygen injection is needed for reactor.

In an embodiment, the reactor is operated at a pressure range of 500 to 900 kPa and a temperature range of 550-700° C.

Herein also disclosed is a method of producing dimethyl ether (DME) comprising introducing one or more feed streams into a reformer to generate synthesis gas, wherein the reformer is a pressurized fluidized bed dry reforming reactor comprising a catalyst and a hydrogen membrane; and converting synthesis gas to DME.

In an embodiment, the hydrogen membrane removes hydrogen contained in the synthesis gas and shifts the equilibrium of the reforming reactions toward completion. In an embodiment, the hydrogen membrane comprises Pd alloy membranes, or Pd supported on ceramics or metals. In an embodiment, the hydrogen membrane is placed vertically in the reformer as hydrogen membrane tubes hanging from the top of the reformer. In an embodiment, hydrogen is collected from the hydrogen membrane tubes via one or more internal manifolds and sent to an external hydrogen collection system.

In an embodiment, the one or more feed streams enter the bottom of the reformer via a manifold or distributor. In an embodiment, the one or more feed streams fluidize the catalyst in the reformer. In an embodiment, the catalyst in the reactor comprises nickel and alumina. In an embodiment, reformed gas exits the top of the reformer and is separated from spent catalyst. In an embodiment, spent catalyst is routed to a regenerator in which the catalyst is regenerated. In an embodiment, regenerated catalyst is returned to the reformer. In an embodiment, the reformer comprises a cyclone for solid gas separation.

In an embodiment, the reformer uses no process water and requires no oxygen. In an embodiment, the reformer is operated at a pressure range of 700-800 kPa and a temperature range of 600-700° C. In an embodiment, this process generates no greenhouse gas emissions. In an embodiment, wherein carbon dioxide recovered from the catalyst regenerator is used as feedstock in the reformer.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION

Figure 1:
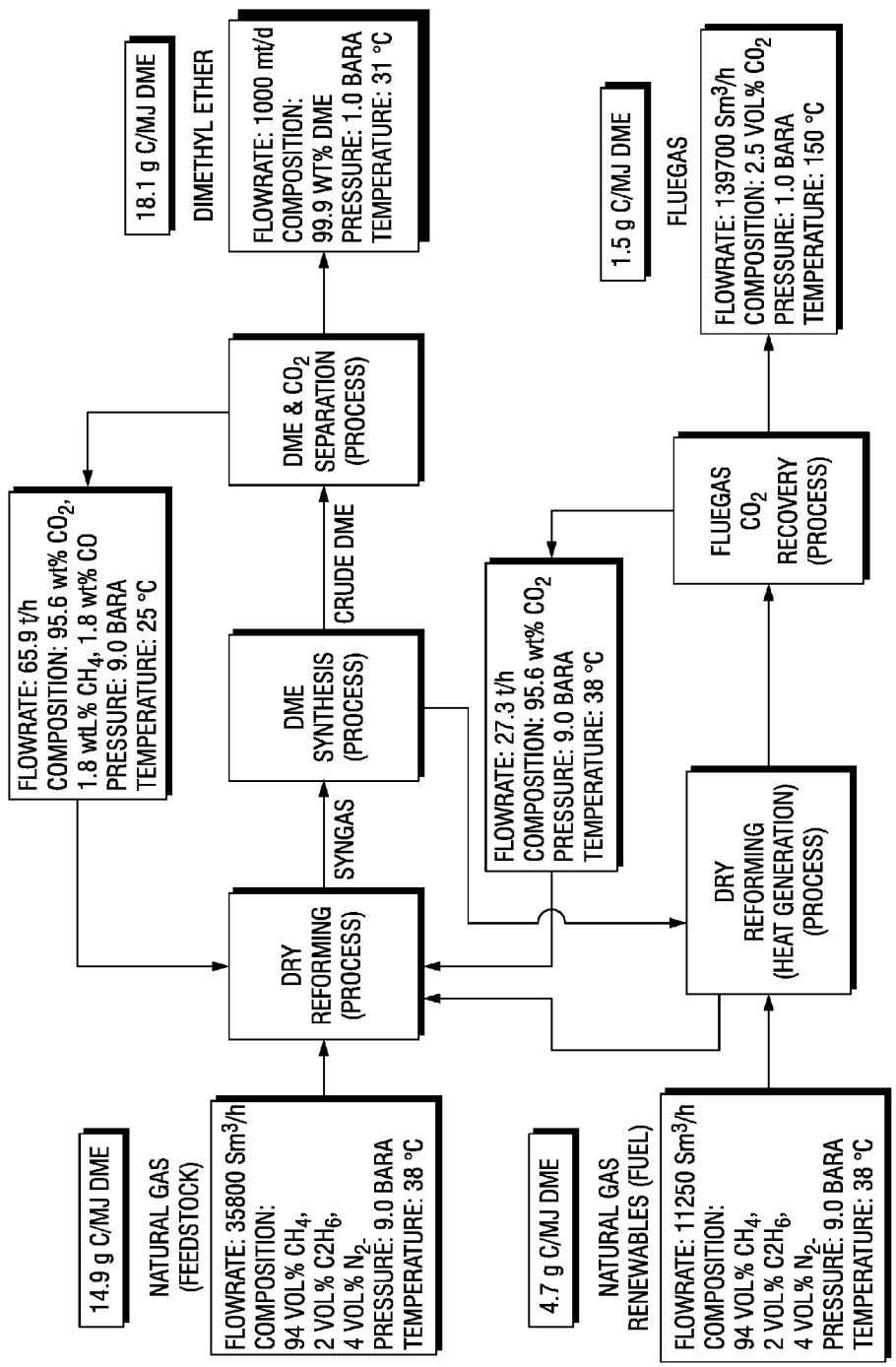
FIG. 1 is a simplified block flow diagram illustrating the process for the production of DME from natural gas, according to an embodiment of this disclosure.

Herein disclosed is a dry reforming reactor comprising a gas inlet near the bottom of the reactor; a gas outlet near the top of the reactor; a fluidized bed comprising a catalyst; and one or more hydrogen membranes comprising palladium (Pd). In an embodiment, the one or more hydrogen membranes comprises Pd alloy membranes, or Pd alloys supported on ceramic or metal substrates. In an embodiment, the one or more hydrogen membranes are placed vertically in the reactor as hydrogen membrane tubes hanging from the top of the reactor. In an embodiment, the hydrogen membranes are configured to selectively collect hydrogen from the tubes via one or more internal manifolds and sent to an external hydrogen collection system.

In an embodiment, the gas inlet is configured to allow one or more feed streams to enter the reactor via a manifold or distributor. In an embodiment, the one or more feed streams fluidize the catalyst in the reactor. In an embodiment, the catalyst in the reactor comprises nickel and alumina. In an embodiment, the reactor is configured to allow reformed gas to exit the top of the reactor and separate from spent catalyst. In an embodiment, no steam or oxygen injection is needed for reactor.

In an embodiment, the reactor is operated at a pressure range of 700-800 kPa and a temperature range of 600-700° C.

Herein also disclosed is a method of producing dimethyl ether (DME) comprising introducing one or more feed streams into a reformer to generate synthesis gas, wherein the reformer is a pressurized fluidized bed dry reforming reactor comprising a catalyst and a hydrogen membrane; and converting synthesis gas to DME.

In an embodiment, the hydrogen membrane removes hydrogen contained in the synthesis gas and shifts reforming reactions toward completion. In an embodiment, the hydrogen membrane comprises Pd alloy membranes, or Pd alloys supported on ceramic or metal substrates. In an embodiment, the hydrogen membrane is placed vertically in the reformer as hydrogen membrane tubes hanging from the top of the reformer. In an embodiment, hydrogen is collected from the hydrogen membrane tubes via one or more internal manifolds and sent to an external hydrogen collection system.

In an embodiment, the one or more feed streams enter the bottom of the reformer via a manifold or distributor. In an embodiment, the one or more feed streams fluidize the catalyst in the reformer. In an embodiment, reformed gas exits the top of the reformer and is separated from spent catalyst. In an embodiment, spent catalyst is routed to a regenerator in which the catalyst is regenerated. In an embodiment, regenerated catalyst is returned to the reformer. In an embodiment, the reformer comprises a cyclone for solid gas separation.

In an embodiment, the reformer uses no process water and requires no oxygen. In an embodiment, the reformer is operated at a pressure range of 700-800 kPa and a temperature range of 600-700° C. In an embodiment, this process generates no greenhouse gas emissions. In an embodiment, wherein carbon dioxide recovered from the catalyst regenerator is used as feedstock in the reformer.

A pressurized fluidized bed (dry) reforming reactor utilizing Pd alloy membranes inserted into the fluidized bed for the purpose of permeating $H_2$ generated in the dry reforming reaction. A hydrocarbon feed stream, containing or co-fed with carbon dioxide, is fed and distributed into the base of the fluidized bed reformer, via a manifold or distributor. The reformer vessel is partially filled with a nickel based catalyst, suitable for dry reforming operating conditions. Reformed gas exits the top of the fluidized bed reformer, where it is separated from the catalyst. Spent catalyst is routed to a regenerator, where the catalyst is regenerated in an oxidizing environment. The regenerated catalyst is returned to the Reformer. $H_2$ produced in the reformer is extracted from the reformer fluidized bed, via multiple vertically oriented palladium alloy supported porous steel tubes, essentially 100% selective to $H_2$, located within the fluidized bed. The permeated $H_2$ is collected from the multiple membrane tubes via internal manifold(s), which route the $H_2$ to an external collection system.

As $H_2$ is permeated from the fluidized bed reformer, the dry reforming equilibria is shifted such that dry reforming reactions can proceed more or less to completion. The $H_2$ permeation facilitates the high degree of dry reforming, without the use of any steam injection into the reformer, at lower reforming temperatures and higher pressures than without the $H_2$ membranes.

Fluidized bed membrane reactors for the purpose of allowing dry reforming reactions to be conducted at higher pressure, lower reaction temperature and without any steam injection have not been disclosed in the art. In various embodiments, such higher pressure refers to pressures above atmospheric pressure and more specifically at pressures above 600 kPa; lower reaction temperature refers to temperatures less than 800° C. The forward equilibrium is favored at temperature above 800° C.

The overall chemical reaction for the process envisaged for the production of Dimethyl Ether (DME) ($C_2H_6O$) from dry reforming of methane and carbon dioxide is: $3\ CH_4 + CO_2 = 2\ C_2H_6O$.

In this process, carbon dioxide is consumed and converted into a useful product DME that can be used as a transportation fuel including as a replacement for diesel.

The dry reforming step uses a fluidized bed reactor with a Ni catalyst to convert methane to syngas. $CH_4 + CO_2 = H_2 + CO$ It is generally not easy to get to a $H_2$ to CO ratio of 1 in the product in practice. Catalysts often coke, deactivate, or are limited in the conversion of methane and result in a lower $H_2$ to CO ratio than desired.

The syngas to DME reaction can be written as: $6H_2 + 6 CO = 2\ C_2H_6O\ (DME) + 2\ CO_2$ In some cases, the fluidized bed dry reforming reactor also contains a hydrogen membrane to preferentially remove hydrogen produced and force the reaction toward full conversion of the $CO_2$ and methane.

This dry reforming process is superior to other routes for the production of DME. It uses less natural gas than competing processes, uses no process water, and requires no oxygen plant, and has significantly lower greenhouse gas (GHG) emissions than the competing processes for DME production.

FIG. 1 shows a simplified block flow diagram for this process. FIG. 1 also illustrates flows and balances for a commercial process for the production of DME from natural gas.

Dry reforming. A pressurized fluidized bed (dry) reforming reactor utilizing Pd alloy membranes, or Pd alloy membranes supported on ceramic or other metal substrates inserted into the fluidized bed for the purpose of permeating $H_2$ generated in the dry reforming reaction. A hydrocarbon feed stream, containing carbon dioxide or co-fed with carbon dioxide, is fed and distributed into the base of the fluidized bed reformer, via a manifold or distributor. The reformer vessel is partially filled with a nickel based catalyst, suitable for dry reforming operating conditions.

Reformed gas exits the top of the fluidized bed reformer, where it is separated from the catalyst. Spent catalyst is routed to a regenerator, where the catalyst is regenerated in an oxidizing environment. The regenerated catalyst is returned to the Reformer. In an embodiment, hydrogen produced in the reformer is extracted from the reformer fluidized bed, via multiple vertically oriented palladium alloy supported on porous steel tubes or ceramic substrates or other metallic substrates, essentially 100% selective to $H_2$, located within the fluidized bed. The permeated $H_2$ is collected from the multiple membrane tubes via internal manifold(s), which route the $H_2$ to an external collection system.

As $H_2$ is permeated from the fluidized bed reformer, the dry reforming equilibria is shifted such that dry reforming reactions can proceed to completion. The $H_2$ permeation facilitates the high degree of dry reforming, without the use of any steam injection into the reformer, at lower reforming temperatures and higher pressures than without the $H_2$ membranes.

Figure 2:
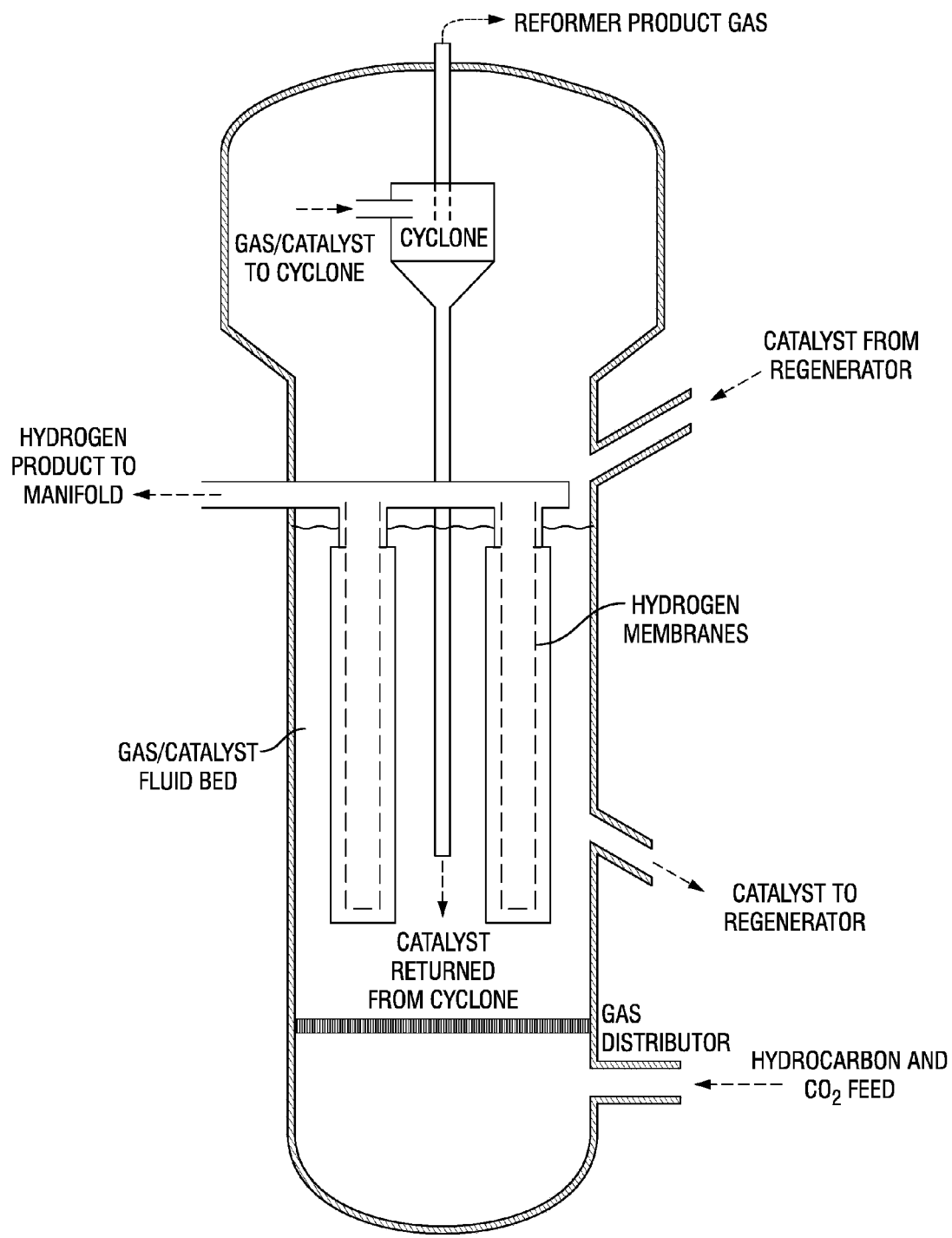
FIG. 2 is a sketch illustrating the configuration of a reformer reactor, according to an embodiment of this disclosure.

Reformer/reforming reactor/reformer reactor. In an embodiment, FIG. 2 shows the configuration of the reformer reactor. The reformer operates at approximately 700° C. at a pressure of 700-800 kPa. Catalyst is fluidized by the incoming methane (or other hydrocarbon) and carbon dioxide feed. The feed gas passes through a gas distributor. The catalyst-gas mixture is in a fluidized bed. Inside the fluidized bed the hydrogen membranes tubes are placed hanging from the top of the reformer. The methane and carbon dioxide are reacted over the fluidized catalyst. The reaction will cause the formation of hydrogen and carbon monoxide via the dry reforming reaction.

In an embodiment, hydrogen will permeate through the membranes and be collected as hydrogen product leaving the reactor. The methane and carbon dioxide will continue to react as some of the hydrogen permeates away producing more hydrogen and carbon monoxide.

In some embodiments, the reformer has a top section that contains a cyclone for solid gas separation. Some amount of catalyst will continue to be transported toward the top of the reactor. The gas/catalyst mixture will enter the cyclone and the solid catalyst particles will separate from the gas and fall back toward the bottom of the reactor. The gas produced leaves the top of the reformer. Catalyst also leaves the reformer through an exit and the catalyst will then proceed to the regenerator. Regenerated catalyst enters the reformer catalyst bed as hot catalyst that supplies heat to the reformer. The catalyst will enter at approximately 900-1000° C. The catalyst residence time in the reformer is in the range of 0.5-4 minutes. The fluidized bed is preferentially operated in turbulent regime. The gas superficial velocity is in the range of 1-3 m/s.

The Nickel catalyst in the reformer with a mean particle size of approximately 200 microns and a nickel content of 2-6 wt % on an alpha alumina support. For use in the system, the catalyst must be fluidizable, generically spherical, and must be attrition resistant during operation. Suitable nickel alumina catalyst is disclosed, for example, in international patent application number PCT/US2005/036588, which is hereby incorporated herein in its entirety for all purposes not contrary to this disclosure and suitable nickel catalyst is disclosed, for example, in U.S. Pat. No. 7,915,196 hereby incorporated herein in its entirety for all purposes not contrary to this disclosure.

Hydrogen Membranes. The addition of the hydrogen membranes to the reformer is optional but preferred. $H_2$ produced in the reformer is extracted from the reformer fluidized bed, via multiple vertically oriented palladium alloy supported on a porous ceramic substrate, essentially 100% selective to $H_2$, located within the fluidized bed. The permeated $H_2$ is collected from the multiple membrane tubes via internal manifold(s), which route the $H_2$ to an external collection system.

Figure 3:
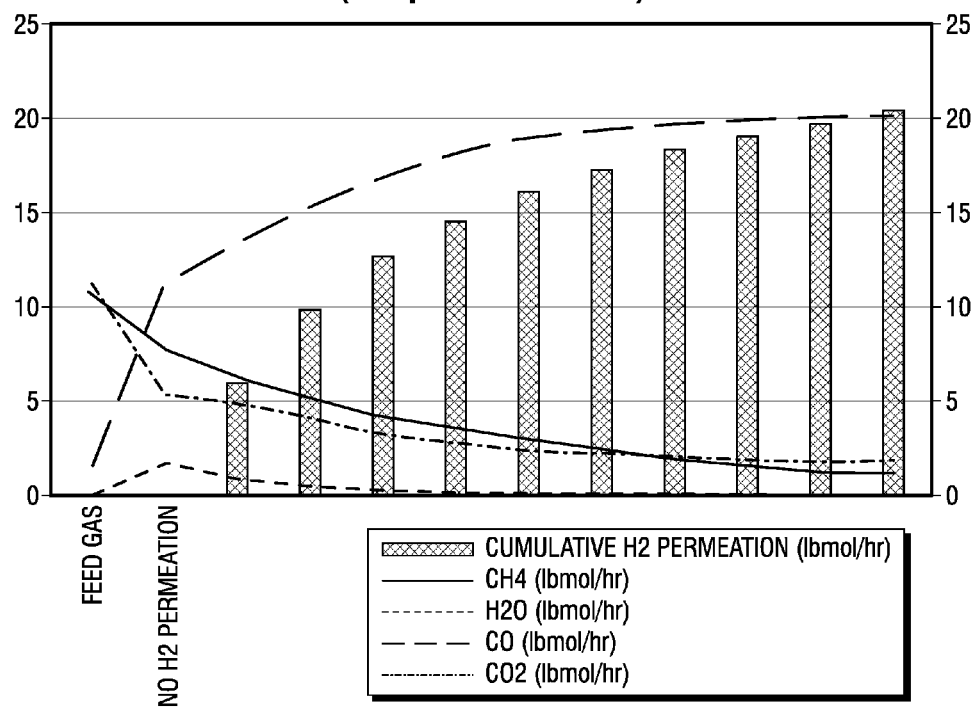
FIG. 3 is a diagram graph illustrating the ability to produce a 1:1 $H_2$:CO syngas at elevated pressure and reduced temperature in the reforming reactor, according to an embodiment of this disclosure.
Figure 4:
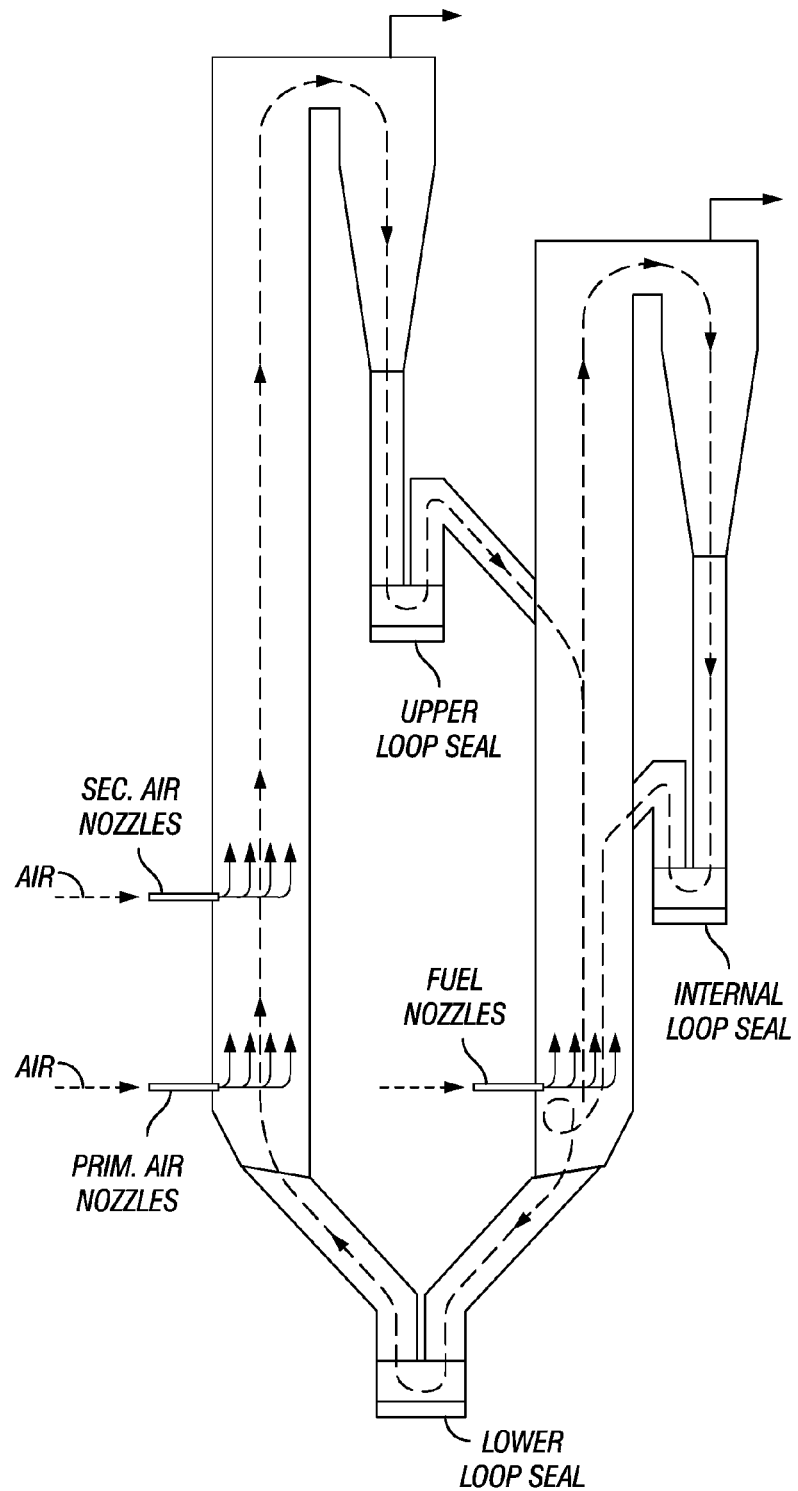
FIG. 4 shows an experimental set up of dry reforming, according to an embodiment of this disclosure.

As $H_2$ is permeated from the fluidized bed reformer (the fuel reactor), the dry reforming equilibria is shifted such that dry reforming reactions can proceed more or less to completion. The $H_2$ permeation facilitates a higher degree of dry reforming, without the use of any steam injection into the reformer, at lower reforming temperatures and higher pressures than without the $H_2$ membranes. FIG. 3 is a diagram illustrating the ability to produce a 1:1 $H_2$:CO syngas at elevated pressure and reduced temperature in the reforming reactor. FIG. 4 shows an experimental set up of dry reforming.

Metallic membranes or metal coated ceramic supported membranes are hung inside the dual fluidized bed reactor, such as Pd or Pd alloy coated cylindrical structures hung inside the fluidized bed reactor or any other suitable structures. Palladium (Pd) based membranes have high hydrogen permeability and an almost infinite selectivity to hydrogen. A thin coating of Pd or Pd alloy 2-50 microns thick (with the minimal thickness being preferred for permeation but slightly thicker membranes desired for long term stability of the membrane) is deposited on the cylindrical support material. Ag, Pt, Au, Rh, Ru, and Pb additives have been added to the Pd to form alloys and improve hydrogen permeability. Self-supporting tubular hydrogen membranes have been successfully scaled up and are also contemplated for use in this catalytic membrane reactor/reformer.

The permeation rate through the hydrogen membranes varies significantly. The hydrogen permeation flux rates can vary from 10-300 NM3 H2/hr/m2 of membrane area with the preferred range of 40-80 NM3 H2/hr/m2. The permeate pressure is relatively low at sub-atmospheric pressure (as low as 1 psia or approximately 7 kPa). The proper choice of the balance between membrane surface area, hydrogen permeation, and overall reactor performance dictate the exact configuration of the reactor/reformer system.

The hydrogen product that goes to the manifold is then compressed and blended back with the reformer product gas to produce a combined syngas with a 1:1 hydrogen to carbon monoxide ratio. In some cases, sweep gas on the permeate side of the membrane is used to increase the flux at a higher pressure and reduce compression costs. If sweep gas is needed or desired, syngas or reformer product gas is used as the sweep gas.

Regenerator. Catalyst from the reformer is sent to the regenerator. The catalyst in the reformer can become deactivated by contaminants or by carbon deposited on the catalyst during the dry reforming reaction. Carbon formation during dry reforming reaction is one of the common problems with dry reforming process that uses a fixed bed. One of the advantages of using a fluidized bed reactor is that the catalyst can be regenerated frequently in air.

In an embodiment, the regenerator operates at approximately 900-1000° C. and catalyst is fluidized by air supplied by an air blower or other means at the bottom of the regenerator. Any carbon on the catalyst is burned off in the regenerator. In one embodiment, the regenerator is a fast fluidized bed where the air and catalyst are mixed at the bottom of the regenerator and the catalyst is conveyed to the top of the regenerator where the catalyst and flue gas are separated out. The superficial gas velocity in the regenerator dense bed is maintained at 1-3 m/s. The hot catalyst then recirculates to the entry nozzle on the reformer. In some embodiments, there is very little or no excess oxygen at the top of the regenerator.

In cases wherein carbon on the catalyst is not sufficient to keep the regenerator at the high temperature needed, supplemental fuel can be burned in the regenerator to heat the regenerator to operating temperature. In one embodiment, a mixer/burner is placed in the regenerator or adjacent to the regenerator vessel. Fuel and air are mixed and burned in the burner with the combustion product gases flowing into the regenerator and supplying any needed heat to the system. In an embodiment, methane is used as the supplemental fuel to the regenerator. In other embodiments, other fuels to the regenerator are used, such as renewable fuels including landfill gas, bio-ethanol, bio-digester gas, pyrolysis oils and liquid fuels, spent glycerol, biomass derived syngas. Alternatively, biomass is used in a biomass boiler where the hot flue gas from the boiler is used to heat the regenerator to operating temperature.

DME Production from Syngas. The hydrogen from the manifold is compressed and blended with the reformer product gas to produce a 1:1 H2/CO ratio syngas. The blended syngas is compressed to approximately 5500 kPa. The blended syngas is reacted to produce primarily a Dimethyl Ether product by this reaction: $6H_2 + 6 CO = 2 C_2H_6O (DME) + 2 CO_2$ In various embodiments, a single step is used to convert syngas to DME. There are multiple-step reactions that can also obtain DME as a product including a first step where syngas is converted to methanol and then methanol is dehydrated to DME. For one step synthesis, a bi-functional catalyst is used that does methanol synthesis and dehydration. There are a number of catalysts that can produce DME, such as mixtures of methanol catalyst (CuO/ZnO/Al2O3) with methanol dehydration catalysts (gamma-alumina). Other bifunctional catalysts such as Ni/Ce-ZrO2/Al2O3, CuO—ZnO—Al2O3 (CZA) over Clinoptilolite, CZA over various zeolites including ferrierite, ZrO2, ZSM-5, NaY or HY, are also used.

In an embodiment, slurry reactors and fixed bed reactors are used to produce DME from syngas. In an embodiment, a multi-tubular fixed bed reactor is used to produce DME from syngas to take advantage of the exothermic DME reaction and to better control reactor temperature and avoid hot spots.

In an embodiment, the conversion reactor has individual tubes of 20-30 mm in diameter filled with catalyst pellets. Syngas passes through the tubes and react to produce DME. In some embodiments, the reactor tubes are placed inside a shell. In some cases, inside the shell and around the tubes, water is circulated to regulate reactor temperature. Through the heat release in the reactor tubes, steam is generated in the shell.

In further embodiments, DME product is recovered from the outlet of the multi-tubular reactor and separated as product. $CO_2$ byproduct, produced in the DME synthesis loop, is separated for recycle to the dry reformer, via conventional distillation. The additional $CO_2$ required to satisfy the dry reforming stoichiometry is recovered from the pressurized regenerator flue gas, using an amine unit with a solvent such as methyldiethanolamine (MDEA). The $CO_2$ is then recycled as feed to the dry reforming reactor.

Figure 5:
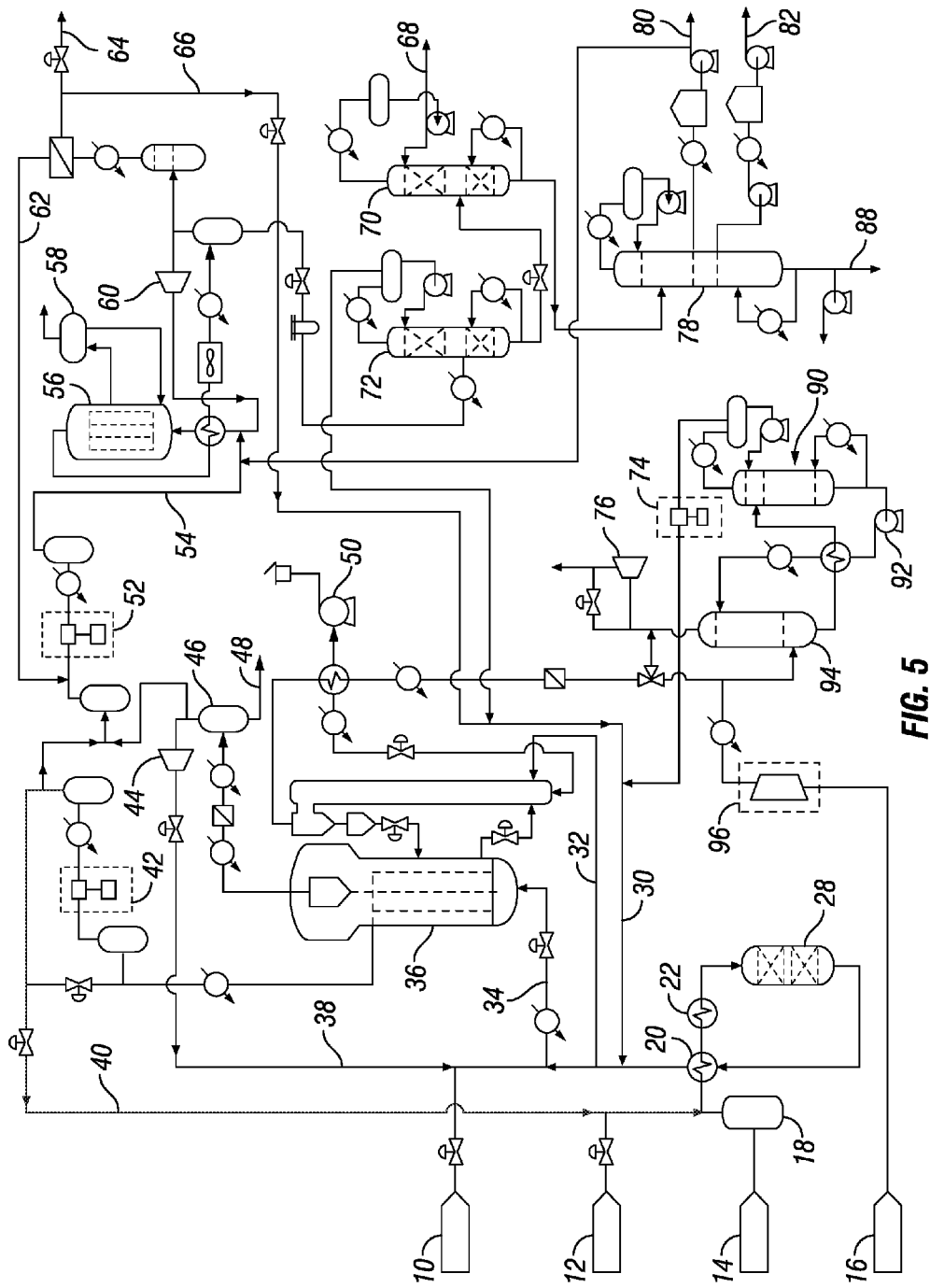
FIG. 5 illustrates an overall process flow sheet for process integration, according to an embodiment of this disclosure.

Process integration. In an embodiment as shown in FIG. 5, the process as described herein is integrated for commercial application. The components in FIG. 5 are explained in Table 1. Other alternative and equivalent arrangements are also possible, which are considered to be within the scope of this disclosure.

TABLE 1

| | |
|---|---|
| 10 | Fluidizing nitrogen |
| 12 | Hydrogen |
| 14 | Natural gas feedstock |
| 16 | External fluegas |
| 18 | Natural gas knockout drum |
| 20 | Hydrodesulfurizer feed/effluent exchanger |
| 22 | Hydrodesulfurizer feed preheater |
| 28 | Hydrodesulfurizer vessel |
| 30 | CO2 plus loop purge |
| 32 | Natural gas fuel |
| 34 | Natural gas plus CO2 feed |
| 36 | Reformer |
| 38 | Recycle gas |
| 40 | Hydrogen |
| 42 | Hydrogen compressor |
| 42 | Reactor effluent |
| 44 | Recycle compressor |
| 46 | Synthesis gas knockout drum |
| 48 | Process condensate |
| 50 | Air compressor |
| 52 | Synthesis gas compressor |
| 54 | Synthesis gas |
| 56 | Converter (DME Reactor) |
| 58 | Converter Steam Drum |
| 60 | Circulator |
| 62 | Hydrogen permeate |
| 64 | Fuelgas |
| 66 | Loop Purge Recycle |
| 68 | Dimethyl ether (DME) |
| 70 | DME Column |
| 72 | CO2 Column |
| 74 | CO2 Compressor |
| 76 | Expander |
| 78 | Methanol Column |
| 80 | Methanol |
| 82 | Fusel oil |
| 88 | Wastewater |
| 90 | Amine Regenerator |
| 92 | Amine Pump |
| 94 | CO2 Absorber |
| 96 | Fluegas Compressor |

TABLE 2

| Parameter | Units | Proposed Dry Reforming Scheme | Alternate Tri-Reforming Scheme (KOGAS) | Alternate Tri-Reforming Scheme (JFE) |
|---|---|---|---|---|
| Natural Gas Consumption (incl. fuel) | MJ (LHV)/liter DME | 25-27 | 26.9 | 27.6 |
| Process Water Consumption | Liter H2O/liter DME | 0 | 0.65 | 0.6 |
| Oxygen Consumption | Kg/liter DME | 0 | 0.69 | 0.67 |
| GHG emissions | G CO2/liter DME | 120-172 | 267 | 272 |

Advantages. The process as described herein has many advantages over existing processes for the production of DME. This process has (1) lower natural gas consumption per liter of DME produced, (2) no process water consumption, (3) no oxygen consumption, and (4) lower greenhouse gas (GHG) emissions per liter of DME produced. The details of these advantages are shown in Table 2 as this process is compared with tri-reforming schemes.

In addition, in this process, the pressurized reformer and regenerator operation facilitates less costly $CO_2$ recovery from the regenerator flue gas. This $CO_2$ roughly balances the net $CO_2$ makeup requirement for the DME synthesis. Hence, the process, as described, does not generate GHG emissions.

The process, as described, is capable of generating a useful 1:1 $H_2$:CO syngas for 100% dry reforming, without the requirement for steam or oxygen injection (as such in bi- or tri-reforming). This syngas quality is then useful for downstream product synthesis, without the need for Water Gas Shift reaction or $CO_2$ removal. The syngas product is available at elevated pressure, which significantly reduces syngas compression horsepower.

The process is able to generate a usable syngas product stream (e.g. 1:1 $H_2$:CO ratio) by dry reforming at elevated pressure and reduced temperature, as compared to other processes. The reduced reformer temperature allows for a drastic reduction in the catalyst circulation in a dual fluidized bed reforming system where the heat for the reforming reactions is supplied by catalyst circulation from a regenerator.

$H_2$ permeable membrane employed in a fluidized bed reformer is able to facilitate 100% dry reforming of a carbonaceous feedstock at elevated pressure and reduced temperature, to produce a useful syngas product. In some embodiments, $CO_2$ recovered from the pressurized catalyst regenerator is used as feedstock in the reformer.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of producing dimethyl ether (DME) comprising
    introducing one or more feed streams into a reformer to generate synthesis gas, wherein said reformer is a pressurized fluidized bed dry reforming reactor comprising a catalyst and a hydrogen membrane inside the dry reforming reactor, wherein said reformer uses no process water and requires no oxygen; and
    converting synthesis gas to DME.

2. The method of claim 1 wherein said hydrogen membrane removes hydrogen contained in the synthesis gas and shifts reforming reactions toward completion.

3. The method of claim 1 wherein said hydrogen membrane comprises Pd alloy membranes, or Pd alloys supported on ceramic or metal substrates.

4. The method of claim 1 wherein said hydrogen membrane is placed vertically in said reformer as hydrogen membrane tubes hanging from the top of the reformer.

5. The method of claim 1 wherein hydrogen is collected from the hydrogen membrane tubes via one or more internal manifolds and sent to an external hydrogen collection system.

6. The method of claim 1 wherein said one or more feed streams enter the bottom of the reformer via a manifold or distributor.

7. The method of claim 6 wherein said one or more feed streams fluidize the catalyst in the reformer.

8. The method of claim 1 wherein reformed gas exits the top of the reformer and is separated from spent catalyst.

9. The method of claim 8 wherein spent catalyst is routed to a regenerator in which the catalyst is regenerated.

10. The method of claim 9 wherein regenerated catalyst is returned to the reformer.

11. The method of claim 1 wherein the reformer comprises a cyclone for solid gas separation.

12. The method of claim 1 wherein the reformer is operated at a pressure range of 700-800 kPa and a temperature range of 600-700° C.

13. The method of claim 1 generating no greenhouse gas emissions.

14. The method of claim 9 wherein carbon dioxide recovered from the catalyst regenerator is used as a feedstock in the reformer.

* * * * *